United States Patent [19]

Matsunaga

[11] Patent Number: 4,528,270
[45] Date of Patent: Jul. 9, 1985

[54] ELECTROCHEMICAL METHOD FOR DETECTION AND CLASSIFICATION OF MICROBIAL CELL

[75] Inventor: Tadashi Matsunaga, Ichikawa, Japan

[73] Assignee: Kabushiki Kaisya Advance Kaihatsu Kenkyujo, Tokyo, Japan

[21] Appl. No.: 546,101

[22] Filed: Oct. 27, 1983

[30] Foreign Application Priority Data

Nov. 2, 1982 [JP] Japan ................................ 57-191802
Mar. 30, 1983 [JP] Japan ................................ 58-52772
Mar. 30, 1983 [JP] Japan ................................ 58-52773

[51] Int. Cl.³ .......................... C12Q 1/04; C12Q 1/06
[52] U.S. Cl. ...................................... 435/39; 204/1 T; 204/403; 435/34
[58] Field of Search .................... 435/34, 39, 173, 36, 435/37, 38, 29; 204/403, 1 T

[56] References Cited

U.S. PATENT DOCUMENTS 3,827,948 8/1974 Hata .................................... 204/1 T
4,055,799 10/1977 Coster et al. .................... 204/403 X

OTHER PUBLICATIONS

David J. Myers et al., Anal. Chem., vol. 45, No. 2, pp. 267-271, Feb. 1973.
Carmen J. Flora et al., Anal. Chem., vol. 52, No. 7, pp. 1013-1020, Jun. 1980.
N. Klein et al., Electroanal. Chem. & Interfacial Electrochem., vol. 61, No. 1, pp. 1-9, (1957).
A. M. Bond et al., Anal. Chem., vol. 47, No. 12, pp. 1906-1909, Oct. 1975.
Tadashi Matsunaga et al., Anal. Chim. Acta., 98, pp. 25-30, (1978).
Tadashi Matsunaga et al., Appl. Environ. Microbiol., pp. 117-121, Jan. 1979.
Tadashi Matsunaga et al., J. Appl. Microbiol, Biotechnol., 10, pp. 125-132, (1980).

Primary Examiner—G. L. Kaplan
Attorney, Agent, or Firm—Finnegan, Henderson, Farabow, Garrett & Dunner

[57] ABSTRACT

An electrochemical method for detecting and classifying microbial cells by applying a sweep potential between a working electrode and a counter electrode while microbial cells are brought into contact with the working electrode and, then, measuring the generated current between the electrodes. Cell numbers and types of cells of microorganisms, animals, and plants are determined from the peak current of cyclic voltammetry.

6 Claims, 12 Drawing Figures

ELECTROCHEMICAL METHOD FOR DETECTION AND CLASSIFICATION OF MICROBIAL CELL

BACKGROUND OF THE INVENTION

1. Field of the Invention

The present invention relates to a novel electrochemical method for the detection and the classification of microbial cells, especially living microbial cells. More specifically, it relates to a novel method for detecting or determining cell numbers (of living cells) or types of cells of, for example, microorganisms, animals, and plants.

2. Description of the Prior Art

The detection of the living cells of microorganisms, animals, and plants is extremely important in, for example, clinical, environmental, and bioindustrial fields. Cell numbers have been heretofore detected by, for example, turbidity methods or micrographical direct counting methods. However, it is difficult to distinguish living cells from dead cells by these methods. Colony counting methods based on colony formation have been used for the detection of living microbial cells. However, these methods are extremely time-consuming (for example, one day or more is required to obtain the detection results) and, furthermore, require complicated and troublesome procedures.

Likewise, classifiable detection or identification of types or kinds of, for example, microorganisms is very important in the clinical test field and various other wide industrial fields. However, extremely troublesome and long term operations are required in the practice thereof, since the classifiable detection or identification is usually based on colony counting methods using so-called selective media or direct counting methods using micrographs.

On the other hand, the present inventors found a phenomenon that a current is generated when living microbial cells are directly contacted with an electrode and reported an electrochemical cell number counting method in Anal. Chim. Acta. 98, 25 (1978); Appl. Environ. Microbiol., 37, 117 (1979); and Eur. J. Appl. Microbiol. Biotechnol., 10, 125 (1980). However, this method still involves problems in that the accuracy of determination is not sufficient and the determination of types of cells and the distinction of microbial properties are not clarified.

SUMMARY OF THE INVENTION

Accordingly, the objects of the present invention are to eliminate the above-mentioned problems in the art and to provide an electrochemical method for detecting and classifying living microbial cells.

Another object of the present invention is to provide a method for determining the cell numbers of living microbial cells.

A further object of the present invention is to provide a method for determining types or kinds of microbial cells.

Other objects and advantages of the present invention will be apparent from the following description.

In accordance with the present invention, there is provided an electrochemical method for detecting and classifying microbial cells comprising the steps of:

applying a sweep potential between a working electrode and a counter electrode while the microbial cells are brought into contact with the working electrode and, then, measuring the generated current between the electrodes.

BRIEF DESCRIPTION OF THE DRAWING

The present invention will be better understood from the description set forth below with reference to the accompanying drawings wherein.

DESCRIPTION OF THE PREFERRED EMBODIMENT

The present inventors have found that not only can cell numbers be counted at an extremely high accuracy but also information capable of detecting types or kinds of microbial cells based on differences between peak potentials can be simultaneously obtained, by applying sweep potential between a pair of electrodes according to various voltammetry methods such as cyclic voltammetry, differential pulse polarograph, phase sensitive A.C. polarograph, and square wave polarograph, while a pair of the electrodes is inserted into a cell suspension, and, then, by measuring the generated current between the electrodes. Especially when a gradually increasing direct current sweep potential and an appropriate minute potential overlapped thereon are applied to a cell suspension according to a differential polarographic, phase sensitive A.C. polarograph, or square wave polarographic method in the presence of 4,4'-bipyridine as a current increasing agent, kinds of microbial cells can be detected or distinguished from each other at an extremely high accuracy by measuring the generated differential current increased by 4,4'-bipyridine. That is, since potentials providing maximum currents obtained from the above methods (i.e., "peak potentials") are different from each other depending upon the types of microbial cells, the distinction or identification of microbial cells can be clearly performed.

The present invention will now be further explained in detail.

Objects To Be Detected

Substantially all living microbial cells of various microorganisms, animals, and plants can be detected according to the present invention. Examples of such cells are those of various microorganisms such as bacteria, actinomycetes, fungi, micro algae, and yeasts; and various cells of animals and plants such as erythrocytes; leukocytes; tumor cells, and cultured animal and plant cells. In this connection, according to the present invention, micrological differentiation or identification as well as microbial cell concentration of various minute organisms can be detected or determined. Furthermore, various wide range distinction such as separation of gram negative and gram positive bacteria, differentiation of revertants or non-revertants in a so-called Ames test and other similar distinctions can be effected according to the present invention, as long as appropriate determination conditions are set.

Determination Conditions and Application Fields

Figure 1:
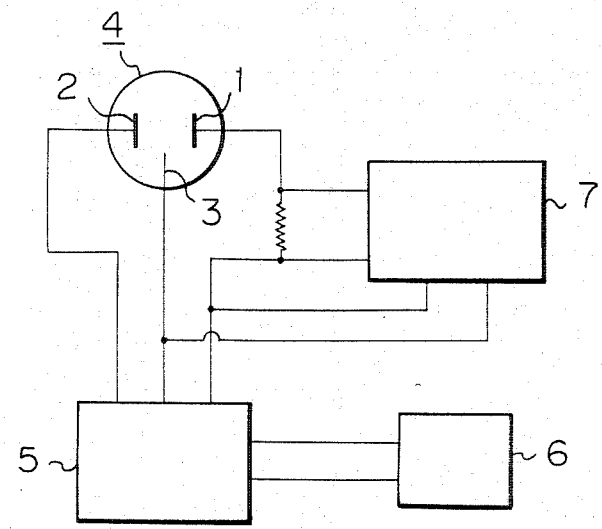
FIG. 1 is a schematic drawing view of one example of a cyclic voltammetry apparatus used in the present invention.

Various conventional voltammetry apparatus can be used in the present invention. A typical example of a voltammetry apparatus is schematically shown in FIG. 1. As shown in FIG. 1, the voltammetry apparatus comprises an electrolysis cell 4 provided with a working electrode 1, a counter electrode 2, and a reference electrode 3 such as a saturated sodium chloride calomel electrode (i.e., "SSCE" hereinbelow), a potentiostat 5, a linear scan or sweep electric source or generator 6, and an X-Y recorder or synchroscope 7. As electrodes, various conventional electrodes such as those made of platinum, gold, silver, and carbon (or graphite), as well as various modified electrodes such as the above-mentioned conventional electrodes coated with polymeric substances can be used. When the potential of the counter electrode 2 is stable and constant, an ordinary circuit system including no reference electrode 3 as used in conventional polarography can be used.

The determination can usually be carried out as follows: That is, a living microbial cell suspension such as a microorganism culture liquid is charged into the electrolysis cell 4, a cyclic scan (or sweep) potential is applied between the electrodes and, then, the generated current is measured. As the sweep potential, a so-called linear sweep changing the potential in proportion to the time is preferably used.

The current-potential curve (i.e., "voltammogram") thus obtained affords not only a maximum current (i.e., "peak current") proportional to a cell concentration but also a peak potential varied depending upon the types of microbial cells, as explained in detail hereinbelow. Thus, information sufficient to identify microorganisms such as bacteria can be obtained based on the specificity of the shape of the curves. Namely, from a practical point of view, the present invention has the following remarkable advantages over the conventional techniques:

(1) More accurate determination can be effected since the response time or the measurement time is remarkably reduced and since various disturbing factors in the electrode reaction can be eliminated due to the use of the sweep potential; and (2) Not only the determination of cell concentrations or cell numbers but also the identification of types of microbial cells can be simultaneously effected. Accordingly, the method according to the present invention is extremely useful as a sensor means for detecting or distinguishing microbial cells in various fields such as a sensor for real time controlling in fermentation processes, determination of microorganism contamination in water, and determination of the numbers of erythrocytes and leukocytes.

Figure 2:
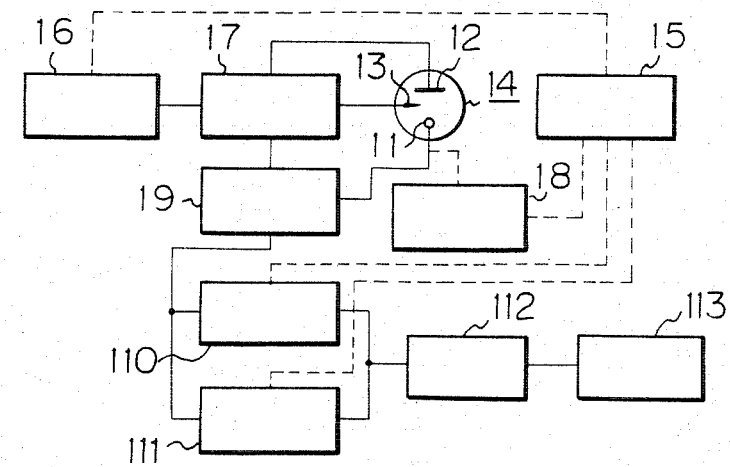
FIG. 2 is a schematic view of one example of a differential pulse polarographic apparatus, especially suitable for use in the distinction of cells according to the present invention.

On the other hand, FIG. 2 schematically illustrates one example of a differential pulse polarographic apparatus, especially useful in the distinction of cells. That is, the apparatus shown in FIG. 2 comprises a cell 14 provided with a working electrode 11, a counter electrode 12, and a reference electrode 13, a pulse sequencer 15, a potential programmer 16, a potentiostat 17, a drop-knocker 18, an i/E converter 19, sample holds ($\tau$) 110 and ($\tau'$) 111, a difference amplifier 112, and a recorder 113. The working electrode 11 and the counter electrode 12 are made of carbon such as basal plane pyrolytic graphite (i.e., "BPG"), high purity graphite for spectroscopy (i.e., "HPG"), platinum, gold, and silver. The reference electrode 13 is a saturated sodium chloride calomel electrode (i.e., "SSCE") or a saturated calomel electrode (i.e., "SCE").

In this case, the determination can usually be carried out as follows: That is, a living microbial cell suspension such as a microorganism culture liquid is charged into the electrolysis cell 14, a gradually increasing scan (or sweep) potential overlapped with a minute potential is applied between the electrodes and, then, the generated current is measured. Usually, a so-called linear sweep in which the potential is varied in proportion to the time is preferably used.

As the minute potential with which the sweep potential is overlapped, those having an appropriate wave shape and cycle capable of providing the desired differential current as mentioned above can be suitably selected.

The voltammograms thus obtained afford peak potentials clearly different from each other depending upon the types of microbial cells. From these peak potential values, the types of microbial cells can be distinguished. Furthermore, information concerning the electrochemical activities of microorganisms such as bacteria can be obtained by analysis of the peak wave shape. Thus, according to the present invention, distinguishment and identification of various bacteria or other microorganisms can be readily accomplished in an extremely short time, as compared with conventional techniques.

As mentioned above, according to the present invention, 4,4'-bipyridine (i.e., "BP") is preferably used as an important activating agent for promoting electron transfer between cells and the electrode. BP participates in the reaction between cells and the electrode by directly adding the BP to a cell suspension or by fitting it to the electrode in such a manner that it is fixed in, for example, nitrocellulose membrane. Although the concentration of BP in the cell suspension may be varied in a wide range depending upon the microbial cells to be detected, BP is generally used in a concentration of a few mM to 100 mM.

When voltammetry is carried out in the presence of BP as mentioned above, the peak current is increased about 1.5 to 2.5 times, the wave shape is clarified and, in the case of the differential current, the peak becomes sharp.

Furthermore, BP can be directly bound to the working electrode as follows: For example, a basal plane pyrolytic graphite electrode with a surface area of 0.17 cm² was prepared. Before modification, the electrode was polished with an aqueous suspension of 0.3 μm of alumina on a polishing cloth. A 1.56 g amount of BP was dissolved in 100 ml of methanol solution. The resulting solution was 100 mM. The graphite electrode was dipped into this solution under slow agitation for 1 minute. The electrode was polished and modified before each run to minimize the undesirable electrochemical signals which arise from surface adsorbed species.

It should be noted that, when cell suspensions sterilized at a temperature of 120° C. for 10 minutes in an autoclave or protoplasts are used in the above-mentioned voltammetry, no peak differential current can be obtained. Accordingly, the phenomenon upon which the present invention depends is specific to living microbial cells.

Furthermore, as is described in Example 9 hereinbelow, any kinds of suitable porous supports, such as a membrane filter, can be used for retaining microbial cells and thereby achieving the close contact between the cells and the working electrode.

Accordingly, when the above-mentioned porous supports are used, a low cell concentration suspension is also detectable by retaining the cells on the porous supports in a high concentration.

Mechanism of Current Generation

Electron transfer from microbial cells to a working electrode is supposed to be closely correlated with the formation and regeneration of coenzymes. Therefore, the peak current seems to be related with metabolic pathway. When, metabolic inhibitors such as rotenone, antimycine, cyanide and arsenite are added to a cell suspension of, for example, *Saccharomyces cerevisiae*. Rotenone, antimycine and cyanide inhibit the mitochondrial electron-transport chain. Although rotenone specifically inhibits electron transfer within nicotinamide adenine dinucleotide (i.e., "NADH") dehydrogenase, antimycine inhibits electron flow between the cytochromes b and c, cyanide blocks electron flow between the cytochrome oxidase complex and $O_2$, the addition of rotenone (7.6 mM), antimycine (5.7 mA) and cyanide (10.8 mA) does not decrease the peak current of the cyclic voltammograms of the cell suspension ($2.4 \times 10^8$ cells ml$^{-1}$). These results suggest that peak current generation is not correlated with the oxidative phosphorylation which occurs inside the mitochondria. Arsenite is known to inhibit pyruvate dehydrogenase. The peak current of the cyclic voltammogram decreases from 4.8 μA to 3.7 μA when 10 mA of arsenite is added to the cell suspension ($2.4 \times 10^8$ cells·ml$^{-1}$). Therefore, the generation of a peak current is correlated with pyruvate dehydrogenase and the citric acid cycle. Then cell wall-bound compounds are eluted by sonicating the whole cells in the buffer solution. The peak current from whole cells decreases. On the other hand, the peak current of the eluent which appears at 0.65 vs SSCE increases gradually. Since sonication does not affect the number of viable cells in the buffer solution, these results indicate that electroactive substances in the cell wall are eluted in the buffer solution with sonication and are electrochemically detected. The absorption of the eluent at 260 nm which is corresponding to the adenine ring also increases in accordance with an increase in the peak current of the eluent when the cell suspension is sonicated. Cofactors such as NADH, nicotinamide adenine dinucleotide phosphate (i.e., "NADPH"), Flavine Mononucleotide (i.e., "FMNH$_2$") and coenzyme A (i.e., "CoA" which have the adenine ring can be electrochemically oxidized. However, the absorption at 340 nm corresponding to NADH and NADPH and absorption at 445–450 nm corresponding to FMNH$_2$ and Flavine-Adenine Dinucleotide (i.e., "FADH$_2$") are not obtained from the eluent. The experimental half wave potential of NADH and NADPH ranges from 0.35 V to 0.75 V vs SCE at carbon electrode. FMNH$_2$ and FADH$_2$ are reported to be electrochemically oxidized at −0.4 V vs SCE. The cyclic voltammograms of NADH and CoA are obtained at the BPG electrode. The peak currents are observed at 0.35 V vs SSCE for NADH and 0.65 V vs SSCE for CoA. The peak potential of CoA is similar to that of the eluent from sonicated cells. Therefore, CoA in the eluent from the sonicated cells is enzymatically determined by the method of Stadtman et al. As a result, 3.6 mM of CoA is detected in the final eluent. The concentration of CoA also increases in accordance with an increase in the peak current of the eluent when microbial cells are sonicated. Therefore, an increase of the peak current obtained from the eluent is attributed to increase of CoA concentration in the buffer solution. On the other hand, as CoA existing in the cell wall is eluted in the buffer solution by sonicating the whole cells, the peak current obtained from the whole cells decreases. These results indicate that the CoA existing in the cell wall mediates an electron transfer between cell and graphite electrode. The peak potential obtained from the eluent, which is similar to that of CoA, is different from that obtained from the whole cells. The peak potential depends on pH and this phenomenon seems to result from a pH difference between the buffer solution and the local environment surrounding the CoA in the cell wall.

EXAMPLES

The present invention now will be further illustrated by, but is by no means limited to, the following examples, in which all percentages are expressed on a weight basis unless otherwise specified.

EXAMPLE 1

*Saccharomyces cerevisiae* (bread yeast; ATCC 7754) was aerobically cultured at a temperature of 30° C. for 8 hours in a medium having a pH of 6.0 and containing 2% of peptone, 2% of glucose, and 1% of yeast extract. After collecting the cultured cells, the cultured cells were washed with a 0.1M phosphate buffer having a pH of 7.0. A cell suspension having a certain concentration and a pH of 7.0 was prepared by suspending the cells obtained above in a 0.1M phosphate buffer. The cell suspension thus prepared was placed in a 15 ml H type cell. After bubbling the cell suspension with air for 10 minutes, a graphite electrode having a diameter of 6 mm was inserted into the cell and, then, the electrochemical behavior of the suspension was observed at a temperature of 25° C. and at a scan rate of 5 mV/sec by a cyclic voltammetry method (see FIG. 1). A platinum wire electrode and a saturated calomel electrode were used as a counter electrode and a reference electrode, respectively. The temperature was 25° C. during the voltammetry operation.

Figure 3:
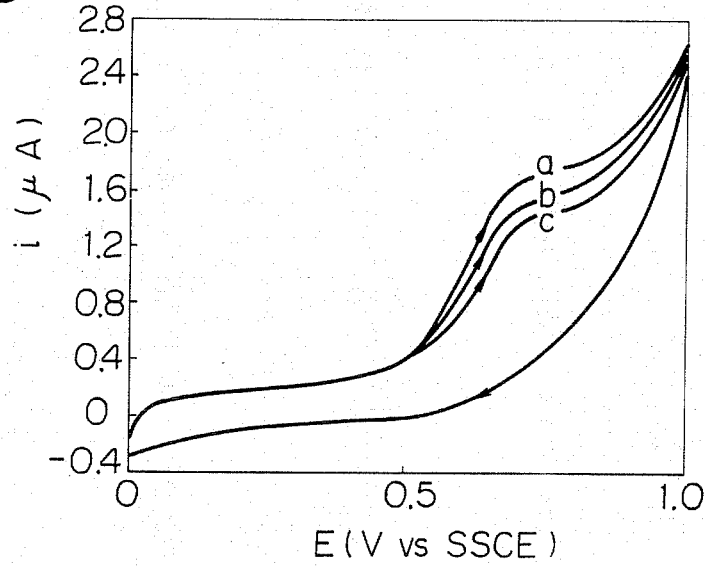
FIG. 3 is a graph illustrating the cyclic voltammograms of a living cell suspension in Example 1.

When the electrodes were inserted into the living cell suspension containing $1.5 \times 10^8$ cells/ml, cyclic voltammograms in each sweep potential as shown in FIG. 3 were obtained. In FIG. 3, i represents a current value (μA), E represents the potential value (V), and a, b, and c are wave curves at a scan rate of 20 mV/sec, 10 mV/sec, and 5 mV/sec, respectively. As is clear from FIG. 3, when a sweep potential of from 0 V to 1 V (vs SSCE) was applied, a peak current appears around 0.7 V. This peak was not observed when the phosphate buffer only was used or when the cell suspension sterilized at a temperature of 110° C. for 10 minutes in an autoclave was used. Furthermore, when the graphite electrode surface was covered with a dialysis membrane so that the electrode would not contact with the cells, no peak was obtained. As a result, it has been found that a peak current can be obtained when living cells are contacted with the electrode.

Figure 4:
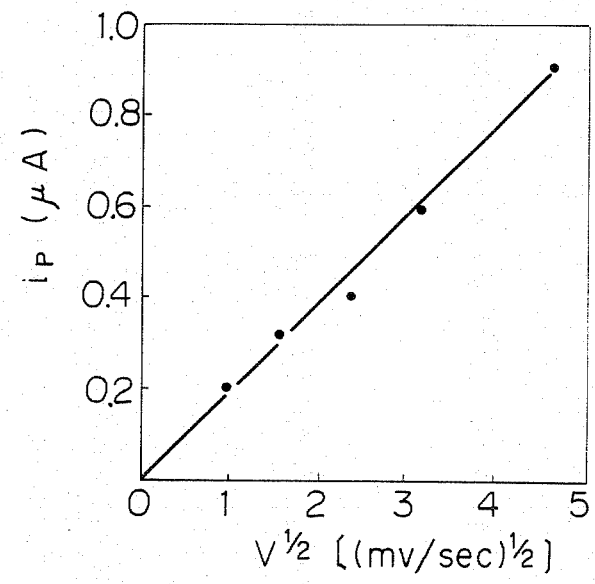
FIG. 4 is a graph illustrating the correlation between the peak currents ip and the square roots of sweep rates of the potential $v^{\frac{1}{2}}$ in Example 1.

On the other hand, when the peak current ip of the cyclic voltammogram detailed above was plotted against the square root of the current scanning rate $\sqrt{v}$ as is shown in FIG. 4, it was found that there was a linear correlation between ip and $\sqrt{v}$. That is, diffusion was apparently the rate-determining stage in the electron transfer reaction between the electrode and the cells and the following relationship was satisfied $$ip \propto Co \cdot v^{\frac{1}{2}}$$

wherein Co is the bulk cell concentration.

Figure 5:
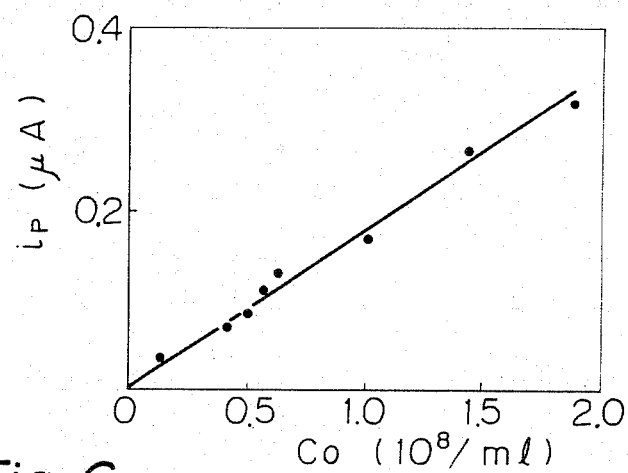
FIG. 5 is a graph illustrating the correlation between the peak currents ip and the cell concentrations Co.

The correlation between the cell concentration Co and the peak current ip is shown in FIG. 5. As is clearly indicated in FIG. 5, there is a linear correlation between ip and Co. Accordingly, it is clear that the cell concentration of the yeast can be determined from the value of ip. The detectable range of the cell concentration was $10^6$ cells/ml to $10^9$ cells/ml which range was sufficient as the range necessary to actually determine the cell concentration in a fermentation operation. Thus, cell numbers in a fermenter can be determined according to the above-mentioned method.

Furthermore, the above-mentioned relationship was obtained in the case of *Lactobacillus fermentum* (i.e., *Lactobacillus fermentum* ATCC 9338), *Bacillus subtilis* (i.e., *Bacillus subtilis* ATCC 6633), *Bacillus* sp., and *Escherichia coli* (the sensitivity, i.e., peak current/cell concentration, was about one tenth that of the yeast in the above-mentioned cases) as well as in human erythrocyte and CHANG LIVER cells (manufactured by Dainippon Pharmaceutical Co., Ltd.) (in these cases, the sensitivity thereof was almost the same as that of the yeast).

EXAMPLE 2

*Saccharomyces cerevisial* ATCC 7754 and *Bacillus subtilis* were aerobically cultured at a temperature of 37° C. for 12 hours in culture media having a pH of 7.0 and the compositions shown in Tables 1 and 2, respectively, in a conventional manner.

TABLE 1

| Glucose | 40 g |
|---|---|
| Peptone | 10 g |
| Yeast extract | 5 g |
| KH$_2$PO$_4$ | 5 g |
| MgSO$_4$ | 2 g |
| Purified water | to 1 liter |

TABLE 2

| Glucose | 10 g |
|---|---|
| Peptone | 10 g |
| Yeast extract | 5 g |
| NaCl | 5 g |
| Purified water | to 1 liter |

The electrodes used in Example 1 were inserted into the culture vessel and the living cell numbers and the peak current ip were real time monitored. The living cell numbers were separately determined by a colony counting method.

The results obtained above are shown in Tables 3 and 4. As is clear from the results shown in Tables 3 and 4, extremely good correlation was observed between the living cell numbers and the peak current ip.

TABLE 3

| Time (hour) | 3 | 5 | 7 | 9 | 12 |
|---|---|---|---|---|---|
| Living cell number ($10^8$/ml) | 0.24 | 0.52 | 1.3 | 3.1 | 4.2 |
| ip (μA) | 0.04 | 0.09 | 0.23 | 0.56 | 0.76 |

TABLE 4

| Time (hour) | 2 | 4 | 6 | 8 | 12 |
|---|---|---|---|---|---|
| Living cell number ($10^9$/ml) | 1.4 | 5.2 | 11.1 | 16.7 | 18.9 |
| ip (μA) | 0.28 | 1.05 | 2.21 | 3.35 | 3.77 |

EXAMPLE 3

Living cells of *Saccharomyces cerevisiae* (i.e., *Saccharomyces cerevisiae* ATCC 7754), *Bacillus sp.*, and *E. coli* were separately suspended in a 0.1M phosphate buffer having a pH of 7.0. Thus, living cell suspensions having concentrations of $1.03 \times 10^9$ cells/cm$^2$, $5.0 \times 10^9$ cells/cm$^3$, and $1.0 \times 10^{10}$ cells/cm$^3$ were prepared.

Figure 6:
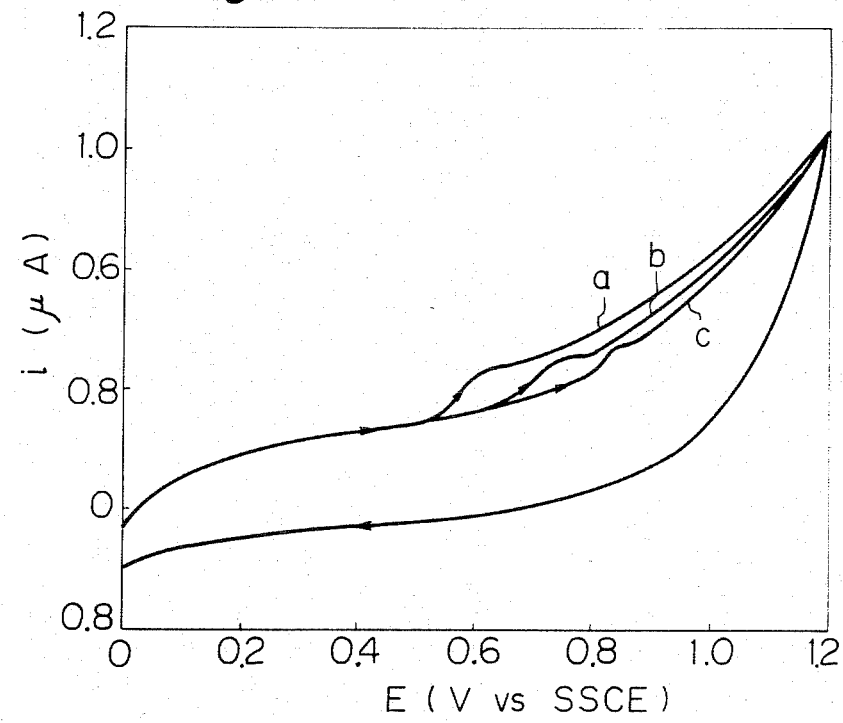
FIG. 6 is a graph illustrating the cyclic voltammograms of cell suspensions in Example 3.

Each cell suspension was placed in electrolysis cells having an electrode surface area of 0.28 cm$^3$ and a cell volume of 15 cm$^3$ and, then, an i-E curve was obtained at ambient temperature (23° C.) at a scanning rate of 10 mV/sec. The results are shown in FIG. 6, wherein curves a, b, and c correspond to the *Saccharomyces cerevisiae*, *Bacillus sp.*, and *E. coli*. As is clear from the results shown in FIG. 6, the potentials at which the peak currents appear are different in the bacteria and, therefore, these bacteria can be clearly distinguished from each other.

EXAMPLE 4

*Bacillus subtilis* IFO 3009 was aerobically cultured at a temperature of 30° C. in nutrient broth containing 1% of meat extract and 1% of peptone. The cultured cells were collected at a log phase and, then, were washed with a 0.1M phosphate buffer having a pH of 7.0. The cultured cells thus obtained were suspended in the same phosphate buffer as was used above to prepare a cell suspension having a concentration of $1.2 \times 10^9$ cells/cm$^3$.

Similarly, *Saccharomyces cerevisiae* (in a YPD medium containing 1% of yeast extract, 2% of polypeptide, and 2% of glucose), *Lactobacillus fermentum* IFO 3071 (in nutrient broth), *Leuconostoc mesenteroides* IFO 3832 (in tomato juice broth containing 1% of tryptone, 1% of yeast extract, and 20% of tomato juice), and *Escherichia coli* (in nutrient broth) were separately cultured at a temperature of 30° C. for 12 hours. The cultured cells were collected at a log phase. The cells thus obtained were suspended in the above-mentioned phosphate buffer to prepare cell suspensions having living cell concentrations of $1.03 \times 10^9$ cells/cm$^3$, $5.0 \times 10^8$ cells/cm$^3$, $1.3 \times 10^9$ cells/cm$^3$, and $1.0 \times 10^{10}$ cells/cm$^3$.

Each living cell suspension was placed in a 15 ml H type cell. Then, differential pulse voltammetry was carried out under the conditions of a scanning potential of 0 to 1.0 V (vs. SSCE), a sampling time of 20 ms, a pulse height potential of 50 mV and 100 mV, a potential sweep rate of 0.5 mV/sec and a determination temperature of 25° C. by using a BPG working electrode, a platinum wire counter electrode and a SSCE reference electrode. A "polarograph type 312" apparatus manufactured by Fuso Seisaku Sho was used.

Figure 7:
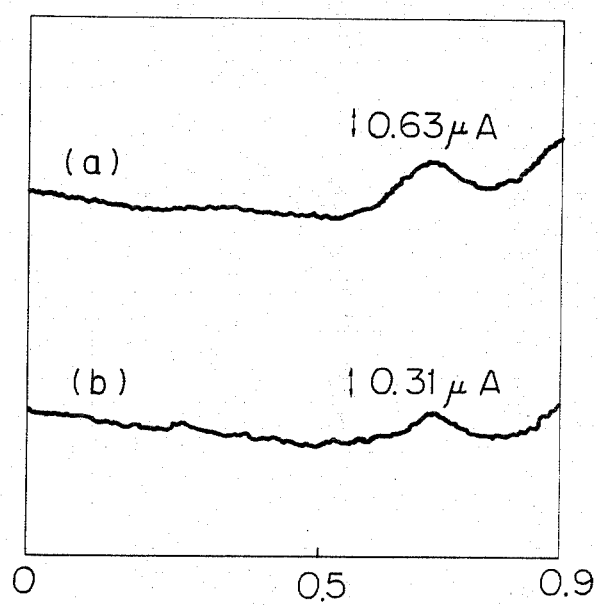
FIG. 7 is a graph illustrating the voltammograms of *Bacillus subtilis* in Example 4.

The voltammograms of *B. subtilis* obtained above are shown in FIG. 7. The very clear peak potentials were observed at 0.68 V (vs. SSCE) as shown in FIG. 7. In FIG. 7, the curves (a) and (b) correspond to the cases of the pulse height of 100 mV and 50 mV, respectively. Furthermore, the peak potentials of the bacteria obtained in the same manner are summarized in Table 5.

TABLE 5

| Microorganism | Peak potential (V vs. SSCE) |
| --- | --- |
| *B. subtilis* | 0.68 |
| *S. cerevisiae* | 0.74 |
| *Lact. fermentum* | 0.75 |
| *Leuco mesenteroides* | 0.80 |
| *E. coli* | 0.85 |

As is clear from the results shown in Table 5, according to the present invention, the types of the bacteria are clearly and readily distinguished from each other. Especially, it should be noted that the gram-negative bacterium, *E. coli*, can be clearly distinguished from the gram-positive bacteria.

EXAMPLE 5

*Salmonella typhimurium* TA 98 and TA 100 were independently cultured in (1) histidine bioassay medium (manufactured by Takara Kohsan Co., Ltd.), (2) a histidine bioassay medium containing 0.075 mM of histidine added thereto, and (3) a histidine bioassay medium containing 0.075 mM of histidine and 0.07 µg/ml of N-methyl-N'-nitro-N-nitroguanidine added thereto. Thus, the variants and the non-variants of TA-98 and TA-100 were obtained.

These microorganisms were independently suspended in a 0.1M phosphate buffer having a pH of 7.0 to prepare cell suspensions each containing $2.1 \times 10^9$ cells/cm$^3$. The differential pulse voltammograms of these cell suspensions were obtained in the same manner as mentioned above.

The peak potential of each cell is shown in Table 6.

TABLE 6

| Cell | his$^+$ | his$^-$ (V vs. SSCE) |
| --- | --- | --- |
| TA 98 | 0.90 | 0.70 |
| TA 100 | 0.92 | 0.60 |

EXAMPLE 6

*Saccharomyces cerevisiae* (i.e., *Saccharomyces cerevisiae* ATCC 7754) was aerobically cultured at a temperature of 30° C. for 8 hours in a medium having a pH of 6.0 and containing 2% of peptone, 2% of glucose, and 1% of yeast extract. The cultured cells were collected and were washed with a 0.1M phosphate buffer. Then, cell suspensions having certain concentrations were prepared by suspending the cells obtained above in the phosphate buffer.

The cell suspension obtained above was placed in a 15 ml H-type cell. After the cell suspension was bubbled with air for 10 minutes, a BPG electrode having a diameter of 6 mm was inserted into the cell and, then, the electrochemical behavior of the cell suspension was observed at a temperature of 30° C. and at a scanning rate of 10 mV/sec by a cyclic voltammetry method (see FIG. 1). A platinum wire counter electrode and an SSCE reference electrode were used.

Figure 8:
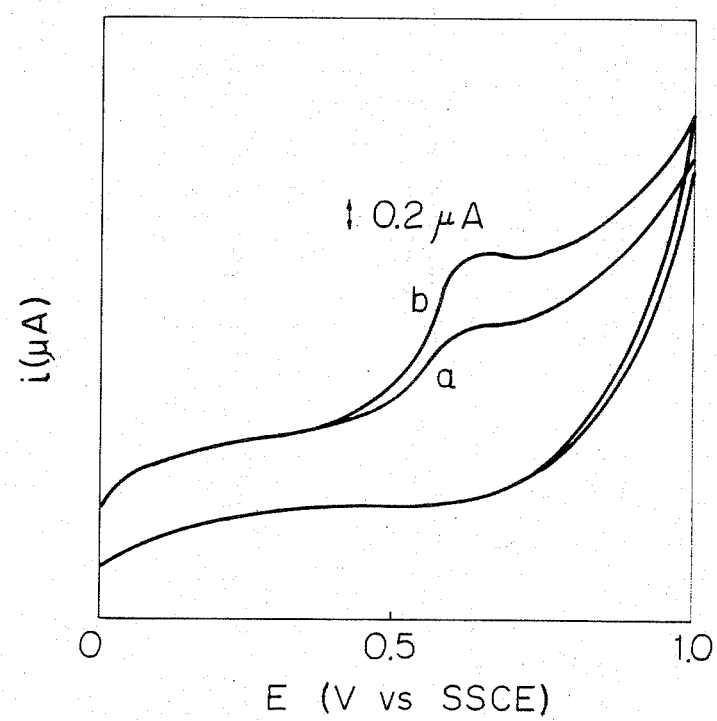
FIG. 8 is a graph illustrating the cyclic voltammograms of a cell suspension in Example 6.

When the electrodes were inserted into the living cell suspension containing $1.5 \times 10^8$ cells/ml, cyclic voltammograms in each sweep potential as shown in FIG. 8 were obtained. In FIG. 8, i represents current (µA), E represents potential (V), and a and b are wave curves in the case of no BP being added and 50 mM of BP being added, respectively. As is clear from the results shown in FIG. 8, when a sweep potential of from 0 V to 1 V (vs. SSCE) was applied, an amplified peak current clearly appeared around 0.7 V especially in the case of BP being added. This peak was not observed when the phosphate buffer only was used or when the cell suspension was sterilized at a temperature of 110° C. for 10 minutes in an autoclave. Likewise, no peak was obtained when the graphite electrode surface was covered with a dialysis membrane so that the electrode would not contact with the cells. As a result, it was confirmed that a peak current can be obtained when living cells are contacted with the electrode.

Figure 9:
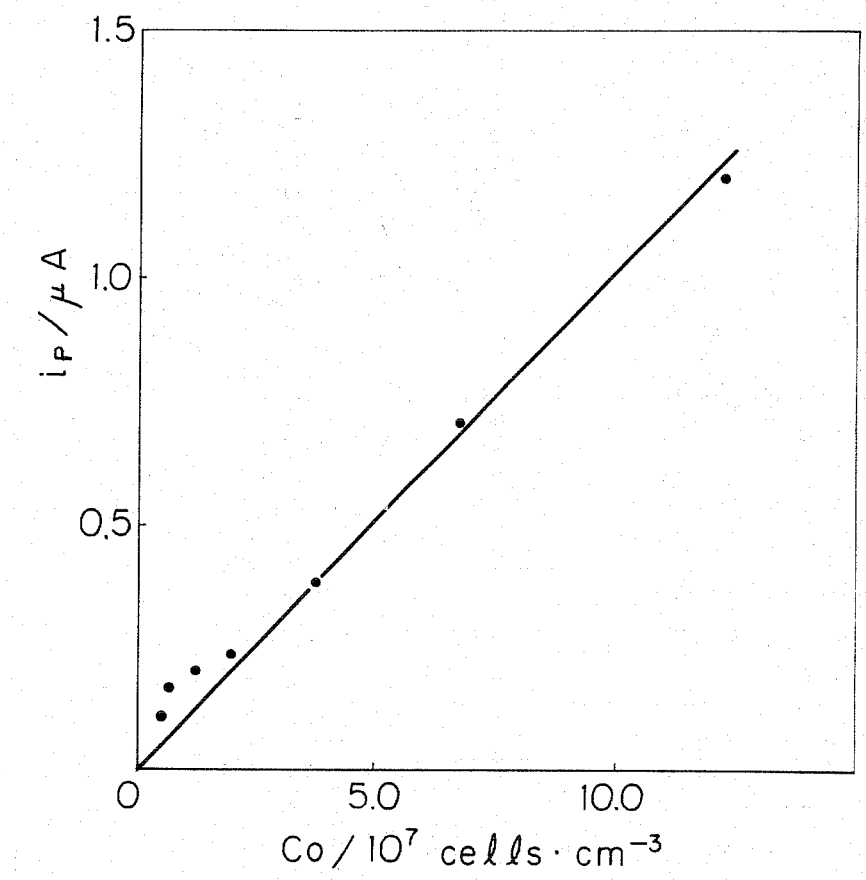
FIG. 9 is a graph illustrating the correlation between the peak currents ip and the cell concentrations Co in Example 6.
Figure 10:
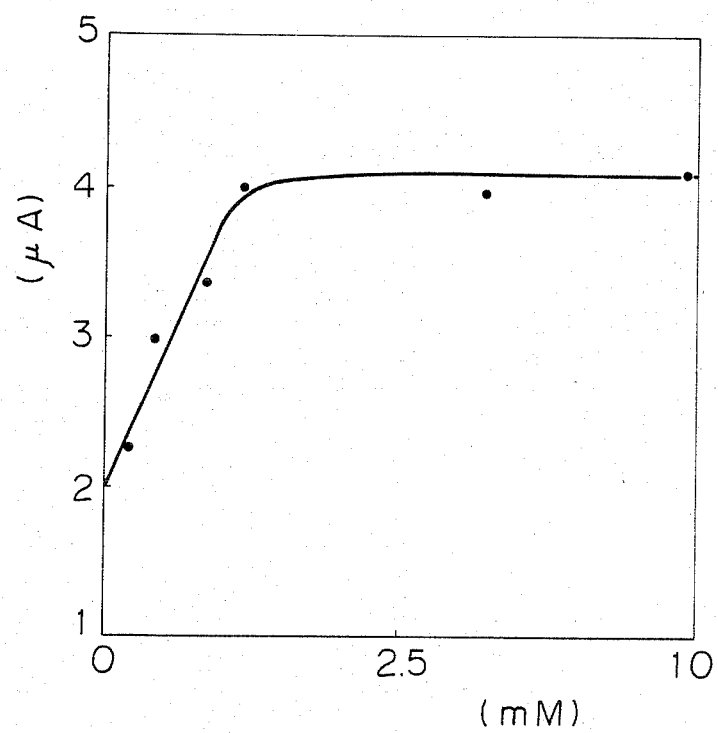
FIG. 10 is a graph illustrating the correlation between the peak currents ip and the 3P concentrations.

FIG. 9 shows the correlation of the cell concentration Co and the peak current ip in the case of the above-mentioned cyclic voltammograms obtained in the presence of 50 mM BP. From the results shown in FIG. 9, it was confirmed that there is a linear correlation between ip and Co. Thus, it is clear that the cell concentration of the yeast can be determined from the value of ip. The detectable range of the cell concentration was $10^6$ cells/ml to $10^9$ cells/ml, which range was sufficient as the range necessary to actually determine the cell concentration in a fermentation operation. Thus, cell numbers in a fermenter can be clearly determined according to the above-mentioned method.

Furthermore, in the case of *Bacillus subtilis* IFO 3009, *Lactobacillus fermentum* IFO 3071, *Leuconostoc mesenteroides* IFO 3832, and *E. coli*, the peak currents were amplified by 1.5 to 2.5 times, in proportion to the BP concentration, and the peak wave shape became sharp in the presence of BP.

EXAMPLE 7

*Saccharomyces cerevisiae* and *Bacillus subtilis* (i.e., *Bacillus subtilis* IFO 3009) were aerobically cultured at a temperature of 37° C. for 12 hours in culture media having a pH of 7.0 and the compositions shown in Tables 7 and 8, respectively, in a conventional manner.

TABLE 7

| Glucose | 40 g |
| --- | --- |
| Peptone | 10 g |
| Yeast extract | 5 g |
| KH$_2$PO$_4$ | 5 g |
| MgSO$_4$ | 2 g |
| Purified water | to 1 liter |

TABLE 8

| Glucose | 10 g |
| --- | --- |
| Peptone | 10 g |

TABLE 8-continued

| | |
|---|---|
| Yeast extract | 5 g |
| NaCl | 5 g |
| Purified water | to 1 liter |

The electrodes used in Example 6 were inserted into the culture vessel, and the living cell numbers and the peak current ip were real time monitored in the presence of 10 mM BP. The living cell numbers were also determined by a colony counting method.

The results obtained above are shown in Tables 9 and 10. As is clear from the results shown in Tables 9 and 10, an extremely good correlation was obtained between the living cell numbers and the peak current ip.

TABLE 9

| Time (hour) | 3 | 5 | 7 | 9 | 12 |
|---|---|---|---|---|---|
| Living cell number ($10^8$/ml) | 0.24 | 0.52 | 1.3 | 3.1 | 4.2 |
| ip ($\mu$A) | 0.08 | 0.18 | 0.47 | 1.13 | 1.51 |

TABLE 10

| Time (hour) | 2 | 4 | 6 | 8 | 12 |
|---|---|---|---|---|---|
| Living cell number ($10^9$/ml) | 1.4 | 5.2 | 11.1 | 16.7 | 18.9 |
| ip ($\mu$A) | 0.50 | 1.89 | 3.98 | 6.03 | 6.78 |

EXAMPLE 8

*Bacillus subtilis* IFO 3009 was aerobically cultured at a temperature of 30° C. in nutrient broth containing 1% of meat extract and 1% of peptone. The cultured cells were collected at a log phase and, then, were washed with a 0.1M phosphate buffer having a pH of 7.0. The cultured cells thus obtained were suspended in the same phosphate buffer as was used above to prepare a cell suspension having a concentration of $1.2 \times 10^9$ cells/cm$^3$.

Similarly, *Saccharomyces cerevisiae* (in a YPD medium containing 1% of yeast extract, 2% of polypeptide, and 2% of glucose), *Lactobacillus fermentum* IFO 3071 (in nutrient broth), *Leuconostoc mesenteroides* IFO 3832 (in tomato juice broth containing 1% of tryptone, 1% of yeast extract, and 20% of tomato juice), and *Escherichia coli* (in nutrient broth) were separately cultured at a temperature of 30° C. for 12 hours. The cultured cells were collected at a log phase. The cells thus obtained were suspended in the above-mentioned phosphate buffer to prepare cell suspensions having living cell concentrations of $1.03 \times 10^9$ cells/cm$^3$, $5.0 \times 10^8$ cells/cm$^3$, $1.3 \times 10^9$ cells/cm$^3$, and $1.0 \times 10^{10}$ cells/cm$^3$.

Each living cell suspension was placed in a 15 ml H-type cell. Then, differential pulse voltammetry was carried out in the presence of 50 mM of BP under the conditions of a scanning potential of 0 to 1.0 V (vs. SSCE), a sampling time of 20 ms, a pulse height potential of 50 mV and 100 mV, a potential sweep rate of 0.5 mV/sec and a determination temperature of 25° C. by using a BPG working electrode, a platinum wire counter electrode and a SSCE reference electrode. The "polarograph type 312" apparatus manufactured by Fuso Seisaku Sho was used.

The peaks of the differential currents thus obtained were extremely clear and sharp and the peak potentials were different from each other depending upon the types of bacteria. The peak potential of each bacterium is summarized in Table 11.

TABLE 11

| Microorganism | Peak potential (V vs. SSCE) |
|---|---|
| *B. subtilis* | 0.68 |
| *S. cerevisiae* | 0.74 |
| *Lact. fermentum* | 0.75 |
| *Leuco. mesenteroides* | 0.80 |
| *E. coli* | 0.85 |

As is clear from the results shown in Table 11, according to the present invention, the types of the bacteria were clearly and readily distinguished from each other. Especially, it should be noted that the gram-negative bacterium, *E. coli* can be clearly distinguished from the gram-negative bacteria.

EXAMPLE 9

Figure 11:
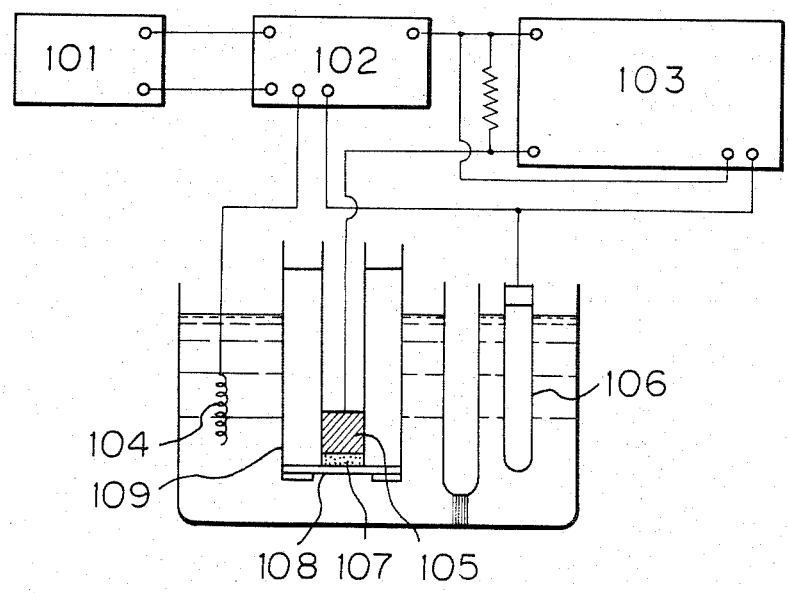
FIG. 11 is a schematic view of one example of an electrode system for detecting microbial cells used in Example 9 according to the present invention.

FIG. 11 shows the electrode system for detecting microbial cells. The electrode system consists of a basal plane pyrolytic graphite electrode 105 (surface area 0.17 cm$^2$), a counter electrode 104 (platinum wire), a reference electrode 106 and a membrane filter 108 for retaining microbial cells 107. Cyclic voltammograms were obtained using a potentiostat 102 (Hokuto Denko Model HA301), a function generator 101 (Hokuto Denko, Model HB104) and a X-Y recorder 103 (Riken Denshi, F 35). Unless otherwise specified, the electrode was polished with an aqueous suspension of 0.3 $\mu$m alumina an a polishing cloth before each run to minimize the undesirable electrochemical signals which arise from surface-absorbed species. The measurement cell was of an all-glass construction, approximately 25 ml in volume, incorporating a conventional three-electrode system. The reference electrode 106 was a potassium chloride saturated calomel electrode. The reference electrode was separated from the main cell compartment by immersion in a glass tube terminated by a sintered glass frit. *Escherichia coli* was cultured at a temperature of 37° C. for 12 hours on the nutrient agar. The cultured cells were suspended in 0.1M phosphate buffer (pH 7.0). Five ml of cell suspension was dropped on a membrane filter (Toyo membrane filter, Type TM-2, nitrocellulose, 0.45 $\mu$m pore size, 25 mm diameter) with slight suction. The microbial cells were retained on the surface of the membrane filter and the filter containing the microorganism was attached to the surface of the graphite electrode. The electrode system was inserted into the phosphate buffer solution and cyclic voltammograms were obtained at ambient temperature (25±2° C.).

Figure 12:
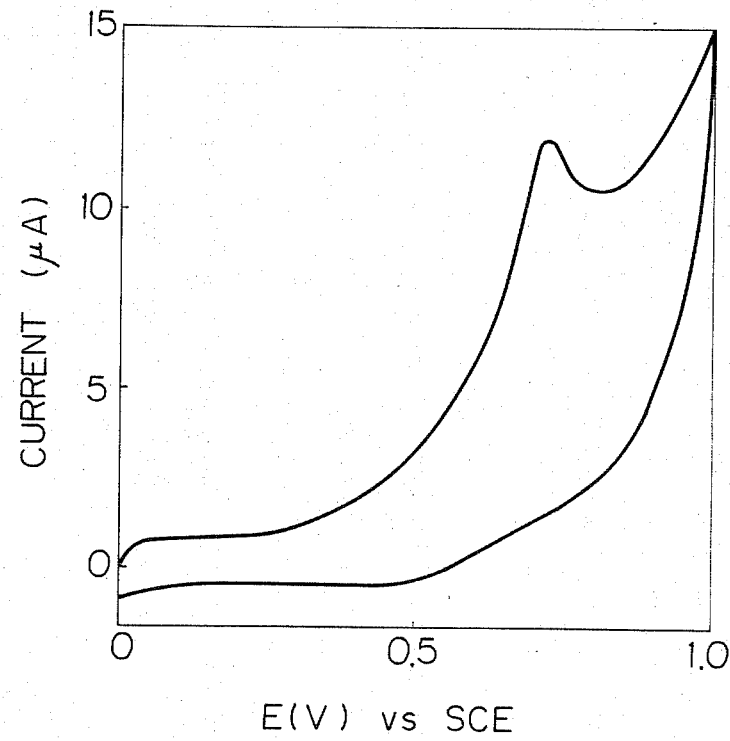
FIG. 12 is a graph illustrating the cyclic voltammograms of microbial cells in Example 9.

FIG. 12 shows the cyclic voltammograms in the potential range of 0 to 1.0 V vs SCE. An anodic wave appeared at 0.72 V vs SCE in the first scan in the positive direction. Upon scan reversal, no corresponding reduction peak was obtained. Therefore, electrode reaction of microbial cells is irreversible.

The peak current was proportional to the cell numbers on the membrane filter in a range of $0.1-1.9 \times 10^9$ cells ml$^{-1}$. These results show that the cell numbers of *E. coli* on the membrane filter can be determined from the peak current of cyclic voltammetry. The minimum detectable cell concentration was $5 \times 10^7$ cells ml$^{-1}$ for *E. coli*.

The peak potentials of cyclic voltammetry of various microorganisms were obtained. The cell numbers on the membrane filters were $6 \times 10^8$ respectively. *Bacillus subtillis* (gram positive), *Lactobacillus fermentum* (gram positive), *Streptococcus sangnis* (gram positive), *Staphylococcus epidermidis (gram positive), *Escherichia coli* (gram negative) and *Salmonella typhimurium* gave peak currents at 0.68 V, 0.68 V, 0.68 V, 0.68 V, 0.72 V. 0.70 V vs SCE, respectively. The plasma membrane of gram-positive bacteria such as *B. subtillis, L. fermentum, Streptococcus sanguis,* and *Staphylococcus epidermidis* was surrounded by a cell wall, typically 250 Å wide, composed of peptidoglycan and teichoic acid. Gram-negative bacteria such as *E. coli* and *S. typhimurium* exhibited a more complex cell envelope. Their plasma membrane was surrounded by a 30 Å wide peptidoglycan wall, which, in turn, was covered by an 80 Å outer membrane that was a mosaic of protein, lipid, and lipopolysaccharide. These results show that the structure of the cell wall affects the peak potentials of cyclic voltammetry. The peak currents of gram-negative bacteria appeared at more positive potentials than these of the above-mentioned gram-positive bacteria.

Further the peak potentials of *Bacillus subtilis* MI 112 (*Basillus subtilis* MI 112 Arg-15 leu B8 thi 5 r$^-$m$^-$recE4 and *Bacillus subtilis* MI 112 (PTL 12) in cyclic voltammetry were also measured according to the following method.

*B. subtilis* MI 112 Arg-15 leu B8 thi 5 r$^-$m$^-$recE4 inoculated into Spizizen Medium (100 ml) and *B. subtilis* MI 112 (PTL 12) inoculated into Spizizen Medium (100 ml) containing Tmp were cultured aerobically at a temperature of 37° C. for 12 hours. The cultured cells were collected and suspended in phosphate buffer solution (pH7) and retained on a membrane filter, which was attached to the surface of the BPG electrode. For the measurement, H type cell, BPG (Basal Plane Pyrolytic Graphite, 0.17 cm$^2$) as the working electrode, platinum wire as the counter electrode, and SCE as the reference electrode were used. Electrochemical behavior of the cells was observed at a temperature of 25° C. and at a sweep rate of 10 mV/sec. The current-potential curves were then obtained.

The result is summerized in the Table 12 below.

TABLE 12

| Peak Potential (V vs SCE) | |
|---|---|
| Plasmids$^-$ | 0.62 |
| Plasmids$^+$ | 0.68 |

I claim:

1. An electrochemical method for detecting and classifying living microbial cells comprising the steps of:
   bringing the living microbial cells into contact with a working electrode;
   applying a sweep potential between the working electrode as an anode and a counter electrode in the presence of 4,4'bipyridine as a current increasing agent; and
   then measuring the generated anodic current between the electrodes to detect an anodic peak current that identifies the presence of living microbial cells.

2. The method of claim 1, wherein said sweep potential and a minute potential which is overlapped on said sweep potential to generate a differential current, are simultaneously applied between the working electrode and the counter electrode.

3. The method of claim 1, wherein the working and counter electrodes are inserted into a suspension of the microbial cells.

4. The method of claim 1, wherein the cell numbers are determined by measuring the value of the peak current of the generated current.

5. The method of claim 1, wherein the types of microbial cells are identified by determining the correlation curve between the generated current and the sweep potential.

6. The method of claim 1, wherein the generated current is measured by applying a cyclic sweep potential between the electrodes.

* * * * *